(12) United States Patent
Pai

(10) Patent No.: US 9,372,194 B2
(45) Date of Patent: Jun. 21, 2016

(54) FLUORESCENT DYES, LABELED CONJUGATES AND ANALYTICAL METHODS

(71) Applicant: Ramdas Pai, Milton, MA (US)

(72) Inventor: Ramdas Pai, Milton, MA (US)

( * ) Notice: Subject to any disclaimer, the term of this patent is extended or adjusted under 35 U.S.C. 154(b) by 0 days.

(21) Appl. No.: 14/573,451

(22) Filed: Dec. 17, 2014

(65) Prior Publication Data

US 2015/0177255 A1 Jun. 25, 2015

Related U.S. Application Data

(60) Provisional application No. 61/964,131, filed on Dec. 23, 2013.

(51) Int. Cl.

| | |
|---|---|
| *C07F 9/576* | (2006.01) |
| *C07F 9/653* | (2006.01) |
| *C07F 9/6541* | (2006.01) |
| *G01N 33/58* | (2006.01) |
| *C07F 9/6561* | (2006.01) |

(52) U.S. Cl.
CPC ............ *G01N 33/582* (2013.01); *C07F 9/6541* (2013.01); *C07F 9/6561* (2013.01); *C07F 9/65324* (2013.01)

(58) Field of Classification Search
CPC ... C07F 9/6561; C07F 9/65324; C07F 9/6541
See application file for complete search history.

(56) References Cited

U.S. PATENT DOCUMENTS

| | | | | |
|---|---|---|---|---|
| 4,039,553 | A | * | 8/1977 | Smith .................. C07D 277/66 544/405 |
| 4,711,955 | A | | 12/1987 | Ward et al. |
| 4,807,237 | A | * | 2/1989 | Ernsting ........... H01S 3/094034 359/339 |
| 5,047,519 | A | | 9/1991 | Hobbs, Jr. et al. |
| 5,316,906 | A | * | 5/1994 | Haugland ............ C07D 235/18 252/62.51 R |
| 5,424,440 | A | | 6/1995 | Klem et al. |
| 5,443,986 | A | * | 8/1995 | Haughland .......... C07D 235/18 252/62.51 R |
| 5,587,112 | A | | 12/1996 | Kauffman et al. |
| 5,696,157 | A | | 12/1997 | Wang et al. |
| 6,635,435 | B1 | | 10/2003 | Conrad et al. |
| 2007/0161055 | A1 | * | 7/2007 | Corry ............... G01N 33/54393 435/7.5 |
| 2014/0206095 | A1 | * | 7/2014 | Strongin ............ G01N 33/6815 436/111 |

OTHER PUBLICATIONS

Zhang et al. Synthesis and antimalarial activity of some indole and benzimidazole amidine derivatives. STN search result; Accession No. 1986:101983, Document No. 104:101983.*

Wang et al. Synthesis of benzimidazole (or benzothiazole-2-yl)-benzzmidine compounds and their NOS inhibitory activity. STN search result, Accession No. 2005:131642, document No. 143:52873.*

* cited by examiner

*Primary Examiner* — Shafiqul Haq
(74) *Attorney, Agent, or Firm* — The John Marshall Law School Patent Clinic; Vangelis Economou

(57) ABSTRACT

There are described novel fluorescent dyes, conjugates which include a radical of a dye and a biological or a synthetic moiety and diagnostic and in vivo assays utilizing such conjugates and other products including the dyes and conjugates.

8 Claims, No Drawings

FLUORESCENT DYES, LABELED CONJUGATES AND ANALYTICAL METHODS

CROSS-REFERENCE TO RELATED APPLICATION

This application is a nonprovisional application of a provisional application, Ser. No. 61/964,131, filed on Dec. 23, 2013, whose disclosure is incorporated by reference in its entirety.

FIELD

Aspects of the invention are directed to novel dye compounds and, more particularly, to novel dye compounds which are useful as fluorescent reporters for use in diagnostic assays, and to labeled conjugates and diagnostic and in vivo assays utilizing the compounds and conjugates.

BACKGROUND OF THE INVENTION

Historically, biomolecules labeled with radioactive isotopes or colorimetric dyes have been employed in bioanalytical procedures. The inherent disadvantages of radioactive labels (safety concerns, disposal costs, record keeping and often poor label stability) and low sensitivity of colorimetric dyes have led to increasing use of luminescent molecules as reporters. Besides having the potential of higher sensitivity than radioactive or colorimetric reporters, luminescent reporters also allow simultaneous detection of multiple analytes, improved stability, reduced costs, improved spatial resolution and greater scope for signal modulation, a feature which permits homogeneous assays to be designed.

Two types of luminescence methods have been employed in bioassays. They are chemiluminescence and fluorescence. Chemiluminescence refers to the transient emission of light during an enzymatic reaction. Fluorescence is the emission of longer wavelength (visible region) of light by a molecule when excited by shorter wavelength (usually in the UV region) of light. If the luminescence is generated by an enzyme, an extra level of amplification is added to the system. Although, chemiluminescence is often regarded as the most sensitive signal system, fluorescence has certain advantages over chemiluminescence. A chemiluminescent molecule can decay only once, giving a single photon, while a fluorophore is continuously excited, having the capacity to emit tens of thousands photons before losing fluorescence due to chemical degradation or photobleaching. Other disadvantages of chemiluminescence include: laborious requirements for use, limitations on sensitivity arising from the transience of chemiluminescence itself, and, the broad spectral emission which precludes the simultaneous detection of multiple analytes in a single sample.

At its limit, fluorescence can detect single molecules either by fluorescence correlation spectroscopy or other methods. However, in practice, the extreme sensitivity potential is limited by interfering signals (noise). These signals may originate from biological components, plastics, reagent impurities, light scattering from particles, background light ("stray" light) which exists in all fluorescence detectors because of the light source used to induce excitation, contamination from a variety of sources, poor aqueous solubility of fluorogenic molecules, significant photoquenching and poor photostability in aqueous solutions and low turnover rates of available fluorogenic substrates by their specific enzymes.

Frequently, in biochemical and immunochemical assays, it is the noise, rather than the instrumentation, that limits sensitivity. As a result, progress in fluorescence has largely been about obtaining selectivity, i.e. improving the signal-to noise ratio. Several techniques have been developed to avoid the noise problem. Time resolved fluorescence, fluorescence correlation spectroscopy and confocal microscopy largely eliminate noise problems since only fluorophores in solution are detected. There is also a trend towards the use of fluorophores that are excited and emit at longer wave lengths where noise sources are less of an issue. Signals from fluorophores with large Stokes' shifts are more easily distinguished from noise.

Unlike a chemiluminescent molecule, a fluorescent molecule can be derivatized so that it can be used either (i) to covalently attach as a fluorescent tag or (ii) as a "fluorogenic" enzyme substrate which can be converted by the action of an enzyme specific for that substrate, into a fluorescent product which exhibits greatly enhanced fluorescence as compared to the starting substrate. The rate or extent to which a substrate for that enzyme has been converted into a detectable chemiluminescent or fluorogenic final product is used to detect or measure the activity of the enzyme.

In biological assays, the activity of an enzyme is used to indirectly detect or measure the quantity of a complementary biological "target". Hydrolytic enzymes such as alkaline phosphatase, β-galactosidase, β-glucuronidase and β-glucosidase have been widely used in conjunction with fluorogenic substrates. These enzymes act on substrate molecules which have been derivatized at hydroxyl moieties to create phosphoric acid, galactoside, glucuronide and glucoside substrates, respectively, and the parent fluorescent molecule. Derivatives of fluorescein, ATTOPHOS® dyes, and BODIPY® dyes are some of the commercially available dyes for this purpose.

U.S. Pat. No. 5,443,986 (Haughland et al.) discloses detecting the activity of enzymes and enzyme conjugates using substrates made from a class of fluorophores generally including quinazolines, benzimidazoles, benzothiazoles, benzoxazoles, quinolines, indolines and phenanthradines.

Kauffman et. al. (Chemical Abstracts, 130: 174202, 1999) discloses p-transfer fluors as shifters for green-emitting scintillating fibers of multi-fiber lengths.

International Patent Application Publication No. WO 00/03034 (Conrad et al.) describes halo-pyrene-disulfonic acids and their derivatives as potential fluorogenic dyes for hydrolytic enzymes. These compounds are described as being highly water soluble, highly stable to non-enzymatic hydrolysis and rapidly converted to the parent fluorescent products (with long wave lengths of excitation and large Stokes' shifts) by the action of appropriate enzymes. This patent also reviews the state of the art as it applies to pyerene derivatves.

U.S. Pat. No. 5,424,440 (Klem et al.) describes several hydroxy benzothiazoles derivatized at the hydroxy group with protective groups that can be cleaved with esterases. The following advantages were described for these compounds: stability in aqueous environment; easily detectable above background interference; highly fluorescent in a variety of solvents; sufficient Stokes' shift; sensitive enough to detect alkaline phosphatase at 10 attomolar concentration; long life time; and some members could be excited with visible light. The fluorogenic phosphates were stable in water and could be hydrolyzed to fluorescent compounds. This patent includes a review of the state of art at the time it was filed.

U.S. Pat. No. 5,587,112 (Kauffman et al.) describes alkaline phosphate substrates derived from 2-benzazolyl dibenzofurans, 2-benzazolyl dibenzothiophenes and 2-benzazolyl carbazoles. These belong to a class of fluorescent compounds called "excited state intramolecular proton transfer" (ESIPT) fluors. The phenomenon of ESIPT fluorescence results in large Stokes' shifts. Solutions of the ESIPT 2-benzazole fluors claimed in the '112 patent absorb strongly in the UV to blue spectral region, i.e., about 420 nm or shorter, with absorption maxima in the UV indicating an extinction coefficient of about 37,000 or greater. These 2-benzazole fluors possess unusually strong, UV stimulated, proton transfer fluorescence in the visible spectral region, having a fluorescence emission peak at about 520 nm or longer at room temperature or above room temperature. These compounds also exhibit fluorescence quantum yields of 0.5 or greater at 300° K.

Molecular Probes, Inc. catalog, 6th Edition, 1996, page 117 lists ESIPT fluor, ELF-97(a quinazolinone) and describes its applications in in situ hybridization, cytological labeling, immunohistochemistry and endogenous phosphate detection. This compound and other quinazolinones, benzothiazoles, benzoxazoles, benzimidazoles, quinolines, indolines and phenanthridines are claimed in U.S. Pat. No. 5,443,986. The preferred fluorogenic substrates described in this patent are said to have the following properties:

a. generally soluble and non-fluorescent in water but capable of releasing a highly fluorescent solid product in an aqueous solution containing the fluorogenic substrate and the specific hydrolase;

b. an excitation maximum of greater than about 340 nm and a Stokes' shift of about 100 nm for the solid product; and c. the fluorescent solid is highly resistant to photobleaching.

Tae-Il Kim et al (Chem. Commun., 5895, 2009) described the synthesis of the phosphate derivative of 2-(2'-hydroxyphenyl) benzothiazole (HBT) as substrate for protein tyrosine phosphatase. HBT is a known ESIPT fluor with a large Stokes shift. However HBT has low quantum efficiency. The compounds claimed in this patent have high quantum efficiencies besides possessing large Stokes shifts, radiation, thermal and chemical stability and good solubility in a wide range of solvents.

As the state of the diagnostic assay art advances there is a continuing need for new fluorogenic dyes which can be activated enzymatically or photolytically and conjugates labeled with novel fluorescent molecules which are useful in diagnostic assays.

SUMMARY OF THE INVENTION

In one aspect of the invention there are provided novel fluorescent dyes which are represented by Formula I

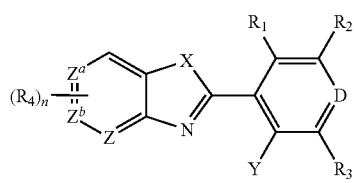

(I)

wherein
D is selected from —C—R$_5$, —C-(A)q-R$_6$, E$^+$(G$^-$), and

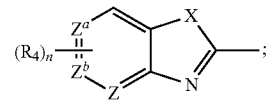

X is selected from oxygen, sulfur, selenium, N—B, and —C(=O)O—;

B is selected from hydrogen, alkyl having from 1 to 10 carbon atoms, aryl, heteroaryl, acyl, aroyl having from 1 to 10 carbon atoms and heteroaroyl having from 1 to 10 carbon atoms);

Z is carbon or nitrogen;

Z$^a$ is selected from carbon, nitrogen and —C-(A)q-R$_6$;

Z$^b$ is selected from carbon, N-alkyl and N-aryl;

A is a divalent linking group having alternating single and multiple bonds such as, for example, —CH=CH—, —C≡C—, CH=CH—CH=CH—, —C≡C—C≡C—, —CH=CH—C≡C—, —C≡C—CH=CH— and the like; or a combination of multiple bonds conjugated with an unsaturated ring system which may be aromatic or heteroaromatic such as, for example,

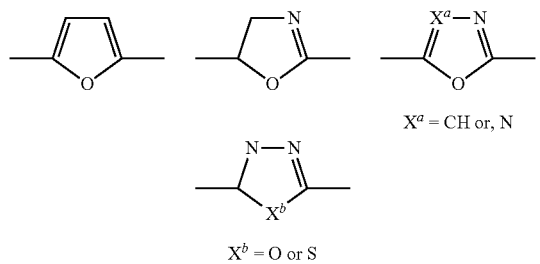

$X^a$ = CH or, N $X^b$ = O or S

E$^+$ is oxygen or N$^+$—R$_7$, where R$_7$ is hydrogen, cyano, alkyl, linear or branched, preferably having from 1 to 10 carbon atoms, arylalkyl, preferably having from 1 to 10 carbon atoms or heteroarylalkyl, preferably having from 1 to 10 carbon atoms;

(G$^-$) is any suitable counterion such as, for example, chloride, cyano, sulfate, sulfonate, trifluoroacetate, phosphate, hexafluorophosphate, tetrafluoroborate, etc.;

Y is a proton transfer group; such as, for example, —OH, NH$_2$, —NHSO$_2$Ar, —NHSO$_2$OH, —NHC(=O)Ar, —NHC(=O)OH, —O(PG), —N(PG)SO$_2$Ar, —N(PG)SO$_2$OH, —N(PG)C(=O)Ar and —N(PG)C(=O)OH;

Ar is an aromatic or a heteroaromatic moiety;

PG is a protective group;

R$_1$, R$_2$ and R$_3$ each independently is selected from hydrogen, an electron withdrawing group and an electron releasing group; or R$_1$ and R$_2$ taken together with the carbon atoms to which they are attached represent the carbon atoms necessary to form a substituted or unsubstituted unsaturated carbocycic or heteroaromatic ring;

R$_4$ is selected from hydrogen, an electron withdrawing group and an electron releasing group;

R$_5$ is selected from hydrogen and a 5 or 6 member aromatic or heteroaromatic ring such as, for example, 4-cyanophenyl or 4-quinolyl, or R$_2$ and R$_5$ taken together with the carbon atoms to which they are attached represent the carbon atoms necessary to form an unsaturated carbocyclic or heteroaromatic ring system such as, for example, a 7,7-disubstituted-7H-indeno[2,1-quinoline ring or a 9.9-disubstituted-9H-fluorene ring;

$R_6$ is

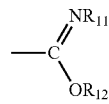

where $R_{11}$ is hydrogen, alkyl, aryl, heteroaryl, $H_2W$ or $R_{13}R_{14}$;
$R_{12}$ is hydrogen, alkyl, aryl or heteroaryl;
$R_{13}$ is hydrogen;
$R_{11}$ and $R_{12}$ taken together with the nitrogen and oxygen atoms to which they are attached represent the carbon atoms necessary to form a substituted or unsubstituted, saturated or unsaturated ring as shown in the examples below.

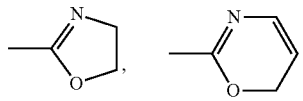

$R_{14}$ is alkyl, aryl or heteroaryl;
W is any suitable anion such as a halide or a sulfate n is an integer of from 0 to 4; and q is 0 or 1, provided that at least $Z^a$ or D is $-C-(A)q-R_6$.

Typical suitable electron releasing groups which are suitable for $R_1$, $R_2$, $R_3$ and $R_4$ include linear or branched chain alkyl ($C_1$-$C_{10}$), methoxy, hydroxyl, amino, ($C_1$-$C_{10}$ alkyl) amino, ($C_1$-$C_{10}$ dialkyl)amino, ($C_1$-$C_{10}$ acyl)amido, ($C_1$-$C_{10}$ aroyl)amido, ($C_1$-$C_{10}$ acyl)oxy, ($C_1$-$C_{10}$ aroyl)oxy, aryl and halogens.

Typical electron withdrawing groups which are suitable for $R_1$, $R_2$, $R_3$ and $R_4$ include nitrile, nitro, $R_8$—C(=O), ($R_8$=$C_1$-$C_{10}$), $Ar^1$—C(=O)($Ar^1$=aryl, heteroaryl), —C(=O)—O—$R_8$, —C(=O)—O—$Ar^1$, —C(=O)—OH, —C(=O)—$NH_2$, —C(=O)—$NHR_9$, —C(=O)—$NR_9R_{10}$, where $R_9$ and $R_{10}$ are each independently alkyl or aryl;

Typical suitable proton transfer groups include —OH, —$NHSO_2Ar$, —$NHSO_2OH$, —NHC(=O)Ar, —NHC(=O) OH, —O(PG), —N(PG)$SO_2Ar$, —N(PG)$SO_2OH$, —N(PG) C(=O)Ar, —N(PG)C(=O)OH and the like. Ar may be substituted with one or more electron releasing or electron withdrawing groups. Typical examples of substituents are methyl and t-butyl groups. Preferred proton transfer groups are those having a pKa between about 5 and about 15 or such a group in which the transferable proton has been replaced with a protective group PG. The proton transfer groups may be photo-cleavable groups. The compounds with a transferable proton are fluorescent while the compounds where this proton has been replaced with a protective group are weakly fluorescent or non-fluorescent. The protective group, PG can be cleaved and a proton substituted in its place by hydrolytic enzymes or by photolysis.

Typical suitable protective (blocking) groups for use as PG include phosphate ($PO_3H_2$), mono and di salt anion of phosphate, mono and di salt anion of sulfate, galactose, sialic acid, glucose, glucuronic acid, amino acids, peptides or the same protected with a blocking group, lipids, nucleic acids, 4-guanidino-benzoate, alkylether derivatives and the like.

These protective groups can be cleaved by enzymes such as alkaline phosphatase, sulfatase, beta-galactosidase, neuraminidase, beta-glucosidase, beta-glucuronidase, various proteases, lipases and nucleases, guanidinobenzoatase, and microsomal dealkylases, respectively. In fluorescence assay literature such enzymes are called "signal enzymes". Amidases and N-dealkylases are examples of signal enzymes that can be used when Y=N(PG)SO2Ar or —N(PG)C(=O) Ar. Typical examples of photo-cleavable protective groups are, 2-nitrobenzyl, alpha-substituted 2-nitrobenzyl (where the alpha substituent is alkyl, aryl, alkoxy, heteroaromatic or alkenyl),2-nitrobenzyloxycarbonyl, alpha substituted 2-nitrobenzyloxycarbonyl, 3,5-dimethoxybenzyloxycarbonyl, α,α-dimethyl-3,5-dimethoxybenzyloxycarbonyl, 3-nitrophenyloxy, 3,5-dinitrophenyloxy and 6-nitroveratryloxycarbonyl. Exposure of the precursor dye to light of appropriate wavelength liberates a pulse of highly fluorescent dye.

When Y is a phosphate group (i.e. Y=—OPO3H2), for example, an enzyme such as alkaline phosphatase can be used to generate the fluorescent 2-hydroxy-4-benzimidic acid ester of the benzazole of Formula I, which has large Stokes shift, high quantum efficiency and radiation and chemical stability. The Stokes shift and fluorescence quantum efficiency of the dyes can be modified by appropriate substitution of the benzene rings.

When Y is a photo-cleavable group the compounds are known as "caged" dyes. The blocked or protected precursors are generally non-fluorescent or weakly fluorescent or fluoresce at substantially shorter wavelengths than those of the corresponding unprotected parent dyes. Exposure of the precursor dye to light of appropriate wavelength liberates a pulse of highly fluorescent dye. The blocked precursor can be added to a sample or sample stream and allowed to reach the target area, but only upon photolysis is the desired fluorescent parent molecule produced in the illuminated area. Following photolysis, the subsequent migration, diffusion, photobleaching, enzymatic conversion to non-fluorescent products or localization of the dye can be observed as a function of the time and location since photolysis. A typical blocking group used for this purpose is o-nitroarylmethine. Upon photolysis, the o-nitroarylmethine group is intramolecularly converted to a derivative of o-nitrosophenone. Hydroxy, amino derivatives of anthracene, naphthalenes, coumarins, fluorescein, resorufin and rhodamine have been protected using the o-nitroarylmethine group.

Some other examples of photolabile groups are, 2-nitrobenzyl, alpha-substituted 2-nitrobenzyl (where the alpha substituent is alkyl, aryl, alkoxy, heteroaromatic or alkenyl), 2-nitrobenzyloxycarbonyl, alpha substituted 2-nitrobenzyloxycarbonyl, 3,5-dimethoxybenzyloxycarbonyl, α,α-dimethyl-3,5-dimethoxybenzyloxycarbonyl, 3-nitrophenyloxy, 3,5-dinitrophenyloxy and 6-nitroveratryloxycarbonyl.

These dyes can be made water soluble by attaching hydrophilic groups such as sulfonic acid or its salts. These water soluble "caged" dyes can then be used in aqueous systems (e.g. physiological fluids) to conduct studies such as flow analysis, velocimetry, analysis of ligand-receptor interactions etc.

Photochemically fluorogenic molecules can also be used in imaging systems. For example, a benzazole of the type shown in Formula 1 protected with a photolabile group can be used in the preparation of printing plates.

DETAILED DESCRIPTION

A preferred group of compounds according to the invention is represented by Formula II

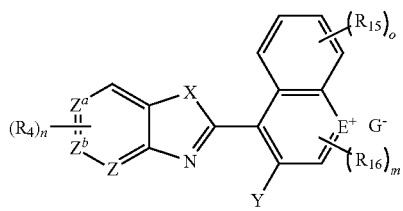

(II)

wherein $R_{15}$ is selected from hydrogen, an electron withdrawing group and an electron releasing group;

$R_{16}$ is selected from hydrogen, an electron withdrawing group and an electron releasing group;

m is 0 or 1;

o is an integer of from 0 to 4; and

E, G, X, Y, Z, $Z^a$, $Z^b$, $R_4$, $R_6$, q and n are as previously defined.

Another preferred group of compounds according to the invention is represented by Formula III.

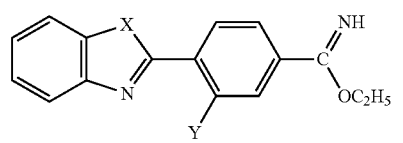

(III)

where X and Y are as previously defined.

Another preferred group of compounds according to the invention is represented by Formula IV

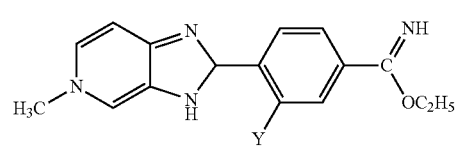

(IV)

where Y is as previously defined

Representative compounds of the invention are:

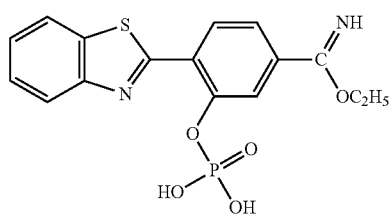

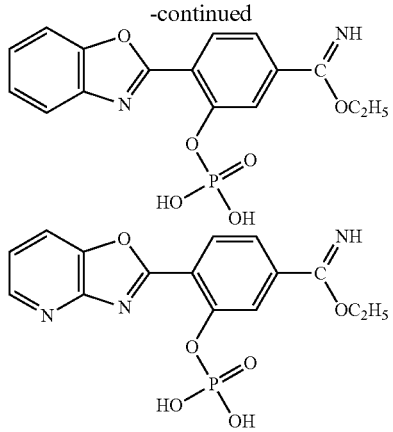

Various of the substituents in the formulas have been defined as being an electron withdrawing or an electron releasing group. It should be noted that the electron withdrawing or electron releasing groups can be modified to include hydrophilic groups to improve the water solubility of the compounds. Typical suitable hydrophilic groups which may be incorporated in the novel fluorescent compounds of the invention are recited together with the definition of "hydrophilic group" below herein.

The fluorophores of the invention described herein belong to the class of ESIPT fluors. These compounds have the advantages of high fluorescence quantum efficiency, large Stokes' shift and high chemical and radiation stability. These compounds have an added advantage since they exhibit intense fluorescence in aromatic hydrocarbons such as benzene and toluene. The fluor released by an esterase from its precursor can be extracted with toluene and its intensity measured in toluene. Since other biomolecules have negligible solubility in toluene there will be no interference due to background noise. By varying the substituents on these compounds their spectral properties can be modified. The ESIPT fluorescent dyes described herein are suitable for the preparation of plastic scintillators which are part of the detector system of particle accelerators and also in liquid scintillation products. Plastic scintillators typically include a fluorescent molecule dissolved in a matrix material which is transparent in at least a portion of the visible electromagnetic radiation spectrum such as polystyrene and are used for the detection and measurement of ionizing radiation. Ionizing radiation, upon striking the matrix material, causes it to emit UV radiation which is absorbed by the fluorescent molecule which then emits visible radiation. Liquid scintillation cocktails contain a fluorescent molecule dissolved in a solvent such as toluene and other additives. Liquid scintillation products are used for measuring radiation emitted by biomolecules labeled with a radioisotope such as 32P (see, for example, U.S. Pat. Nos. 5,298,189; 5,552,551 and 5,587,112).

Fluorescent dyes are widely used as tracers for localization of biological structures by fluorescence microscopy, for quantification of analytes by fluorescence immunoassay, for flow cytometric analysis of cells, for measurement of physiological state of cells, for quantification assays such as DNA sequencing, and other applications (Haugland et al., U.S. Pat. No. 5,442,045). Fluorescent dyes are also used for the determination of ions like Calcium and gases like nitric oxide The isothiocyanate derivatives of these dyes can also be used for protein/peptide sequencing by the Edman degradation procedure (see Jin, S. W. et al., FEBS Lett. 150, 198, 1986; Hirano, H. et al., Biol. Chem. Hoppe-Seyler, 1259, 367, 1980).

In another aspect of the invention there are provided labeled conjugates comprising a radical of a dye molecule of Formulas I-III and a radical of a biological/synthetic (organic, inorganic) moiety. These fluorescent conjugates (probes, labels) are made by attaching chemically reactive fluorescent dyes to reactive sites on a wide variety of materials, both organic and inorganic. Although the biological/synthetic moiety may be attached at various positions on the dye moiety the preferred points of attachment are at the $R_1$, $R_2$ and $R_3$ positions (Formula I) and the various substituents in Formulas II-IV.

The attachment of the biological/synthetic moiety to the linkage through which it is attached to the dye, or to the dye, may be through any appropriate position on the biological/synthetic moiety which will not negatively affect the intended function of the biological/synthetic moiety.

Generally, the novel conjugates of the invention include at least one biological/synthetic moiety which can be attached directly to the dye or which can be attached to the dye through a divalent achromophoric linking group. By the term "achromophoric linking group" is meant one which does not cause any appreciable shift in the spectral absorption characteristics of the dye moiety. The linkage should be non-conjugated. The linking group may also have a chelating group.

The selection of the covalent linkage to attach the benzazoles to the conjugated substance typically depends on the functional group on the substance to be conjugated. The types of functional groups typically present on the organic or inorganic substances include, but are not limited to, amines, thiols, alcohols, phenols, aldehydes, ketones, phosphates, imidazoles, hydrazines, hydroxylamines, disubstituted amines, halides, epoxides, sulfonate esters, purines, pyrimidines, carboxylic acids, or a combination of these groups. A single type of reactive site may be available on the substance (typical for polysaccharides), or a variety of sites may occur (e.g. amines, thiols, alcohols, phenols), as is typical for proteins. Although some selectivity can be obtained by careful control of the reaction conditions, selectivity of labeling is best obtained by selection of an appropriate reactive dye.

Typical functional groups which are useful as coupling groups which can be attached to the dye molecule, and the substituents of the biological/synthetic moiety with which such coupling groups can be reacted to provide the achromophoric linking group within the labeled conjugate are listed in Table I.

TABLE I

| Coupling Group | Substituent |
| --- | --- |
| N-hydroxysuccinimide esters | amino esters (α-amino, lysine) |
| Imidoester | amino groups |
| Aldehydes | amino groups |
| Mixed anhydrides | nucleophilic groups |
| Isothiocyanates | nucleophilic groups |
| 2,4-Dichloro-5-triazine | nucleophilic groups |
| Diazonium salts | tryptamine, histamine |
| Bromoacetyl | histamine, -SH |
| Maleimido | -SH |
| Activated disulfide bonds (e.g., 2-pyridyldisulfides) | -SH |
| Azides, diazirinyl, azidoaryl | amines, anilines |

A more detailed list of coupling groups appears in U.S. Pat. No. 5,696,157.

Many other linking groups may be incorporated into the labeled conjugates of the invention. For example, the hydrophilic groups mentioned above are substantially achromophoric and certain of these can be derivatized and utilized as suitable linking groups. For example, an —$NH_2$ group can be converted to an amide as a result of attaching the biologically active moiety ("BIO") to it, i.e., —NHCO-BIO. Further, in another embodiment a hydrophilic group may be attached to the linking group. For example, in the case of a primary amine one of the hydrogen atoms is replaced by a biologically active moiety attached to it as described above and the other hydrogen atom can also be replaced by a hydrophilic group such as, for example, —$(CH_2)_2PO_3H_2$. Thus, it will be appreciated that the linking group, while serving as the means for attaching the dye moiety to the biologically active moiety, can also have a hydrophilic group attached to it. In addition, the linking group may also function as a hydrophilic group such as, for example, in the case of —NH, -BIO and —$P_2(OH)$-BIO. Solubilizing groups may also be attached to suitable positions on the dyes. The presence of such solubilizing groups can help to avoid undesirable nonspecific binding of the conjugates to components present in biological fluids such as, for example, plasma proteins.

The fluorescent dyes and labeled fluorescent conjugates of the invention may be used in various applications including diagnostic assays which are based on an energy transfer to fluorescent label and assays which are based on enzymatic attack on the conjugate to release the fluorescent moiety, in vivo imaging applications, analytical methods, etc. In medical imaging techniques, e.g., X-ray imaging, positron emission tomography (PET), ultrasound imaging and magnetic resonance imaging (MRI), a narrow band frequency radiation illuminates an object of interest to produce reflected or emitted radiation which is then gathered from the object by a detector. The reflected or emitted radiation is then processed by an imaging algorithm to obtain useful information about the object. The use of ionizing radiation in imaging, for example, with X-rays involves significant health risks to a patient when the patient is exposed to the radiation for prolonged periods of time or in multiple imaging schemes. Furthermore, certain of these imaging techniques undesirably involve the use of invasive procedures which are both costly and painful. Yet other techniques such as MRI do not yield consistently useful results. Imaging techniques involving measurement of light emitted by fluorescent molecules localized in an organ afford non-invasive, safe and relatively fast methods for selectively highlighting in vivo biological targets, biomarkers and pathways that underlie disease progression and therapeutic response. In practice the fluorescent molecules alone or the fluorescent conjugates are injected into a patient. The moiety attached to the fluorescent dye radical in the conjugate can assist in targeting the fluorescent molecule to a specific particular site. See, for example, U.S. Pat. Nos. 6,304,771 and 7,303,741.

With these synthetic probes, ligands are frequently used to confer a specificity for a biochemical reaction that is to be observed and the fluorescent dye provides the means of detection or quantitation of the reaction. The ligand is usually a member of activate the a pair of molecules that can bond together with a high degree of specificity. Examples of specific binding pairs are shown in Table II. Binding pair members present in animal cells, plant cells, bacteria, yeast or viruses can be detected with fluorescent probes. The complementary member may also be immobilized on a solid or semi-solid surface such as a polymer, polymeric membrane or polymeric particle. The fluorescent dye may also have a protective group PG which can be cleaved enzymatically or by photolysis after binding to the complementary member (see, for example, U.S. Pat. No. 5,696,157 to Haughland).

TABLE II

| Antigen | Antibody |
|---|---|
| Biotin | Avidin (or streptavidin or anti-biotin |
| IgG | Protein A or Protein G |
| Drug | Drug receptor |
| Toxin | Toxin receptor |
| Carbohydrate | Lectin or carbohydrate receptor |
| Peptide | Peptide receptor |
| Protein | Protein receptor |
| Enzyme substrate | Enzyme |
| DNA (RNA) | aDNA (aRNA)* |
| Hormone | Hormone receptor |
| Ion | Chelator | aDNA and aRNA are the antisense strands used for hybridization.

In general, it is desirable that fluorescent labels for use in such assays have a relatively long emission wavelength, e.g., above 500 nm. In addition, it is desirable that the labels have a large Stokes shift, be stable under the assay conditions, be relatively free of non-specific interference both from materials in solution and the moiety to which the label is conjugated and exhibit high quantum yields. Also, it is desirable to have dyes whose fluorescence is not quenched in aqueous solutions.

Useful dye-conjugates of the present invention include conjugates of biomolecules (antigens, haptens, an Fab fragment, amino acids, peptides, proteins, nucleic acids, nucleic acid polymers, carbohydrates, lipids), drugs, vitamins, metabolites, toxins, environmental pollutants, pesticides, ion-complexing moieties, cells or cellular components.

Alternatively, the conjugates of the present invention are conjugates of cells, cellular systems, cellular fragments or sub-cellular particles. Typically, in this embodiment of the invention the conjugated materials include virus particles, bacterial particles, virus components, biological cells (such as animal cells, plant cells, bacteria or yeast) or cellular components.

In one embodiment of the invention, the conjugated substance is an amino acid or a polymer of amino acids such as a peptide or protein. Amino acids mean natural amino acids or their optical isomers, as well as synthetic variations utilized in the art. Common synthetic variations include amino acids that are protected on their amino, carboxylic acid, hydroxyl, thiol, imidazole or other functional group. Other modified amino acids are substituted by phosphate, or through glycosylation or acylation with a $C_1$ to $C_{22}$ carboxylic acid. Peptides generally have molecular weights of less than about 5,000 to 10,000 daltons, and proteins have molecular weights greater than about 5,000 to 10,000 daltons and typically possess secondary, tertiary and/or quaternary structure. Preferred conjugates of peptides contain at least five amino acids, more preferably 5 to 36 amino acids. Preferred peptides to be conjugated to the dyes of the invention include, but are not limited to, neuropeptides, chemotactic peptides, cytokines (such as lymphokines), gastrointestinal peptides, toxins, protease substrates, synthetic peptides, experimental peptides, endothelin and protein kinase substrates. Protein conjugates of the invention include labeled enzymes, antibodies, catalytic antibodies, kinases, lectins, glycoproteins, histories, albumins, lipoproteins, avidin, streptavidin, protein A, protein G, phycobiliproteins, hormones, toxins and growth factors. Typically, the conjugated protein is an antibody, an antibody fragment, avidin, streptavidin, α-bungarotoxin, a lectin, a growth factor, or a phallotoxin.

In another embodiment of the invention, the conjugated substance is a single nucleic acid base, single nucleoside, single nucleotide or a nucleic acid polymer. A nucleotide comprises an ester of a nucleoside and one or more phosphoric acid or polyphosphoric acid groups, optionally containing an additional linker or spacer for attachment of a fluorophore or other ligand, such as an alkynyl linkage (U.S. Pat. No. 5,047,519 to Hobbs, Jr. et al., (1991), incorporated by reference), an aminoallyl linkage (U.S. Pat. No. 4,711,955 to Ward et al. (1987), incorporated by reference) or other linkages. Nucleotides, as used herein, include natural and synthetic derivatives, including deoxynucleotides, dideoxynucleotides, cyclonucleotides and abasic nucleotide analogs, wherein the base is replaced by a fluorophore or hapten. Preferably, the conjugated nucleotide is a mono-, di- or triphosphate ester of an adenosine, a guanosine, a uridine, a cytidine or a thymidine. More preferably, the conjugated nucleotide is a nucleoside triphosphate or a deoxynucleoside triphosphate or a dideoxynucleoside triphosphate.

Preferred conjugates of nucleic acid polymers are labeled oligonucleotides composed of fewer than 50 nucleotides, more typically composed of fewer than 25 nucleotides. Oligonucleotides are optionally deoxyribonucleic acid polymers (DNA) or ribonucleic acid polymers (RNA), or a hybrid thereof. Nucleic acid polymers are optionally single-stranded or multi-stranded; and may be a natural polymer (biological in origin) or a synthetic polymer (modified or prepared artificially). The nucleic acid polymer optionally incorporates an unusual linker such as morpholine derivatized phosphates (Antivirals, Inc., Corvallis Oreg.), or peptide nucleic acids such as N-(2-aminoethyl)glycine units (Wittung, et al., NATURE 368, 561 (1994)). In one embodiment of the invention, the dye is attached to the nucleotide, oligonucleotide or nucleic acid polymer via one or more purine or pyrimidine bases through an amide, ester, ether or thioether bond. In another embodiment of the invention, the dye is attached to the phosphate or carbohydrate by a bond that is an ester, thioester, amide, ether or thioether.

In another embodiment of the invention, the conjugated substance is a carbohydrate, i.e. an organic compound composed of carbon, hydrogen and oxygen and occasionally nitrogen or sulfur, that include sugars, starches and celluloses. The conjugated substance is typically a polysaccharide, such as dextran, FICOL, heparin, glycogen, amylopectin, mannan, inulin, starch, agarose and cellulose, all of which are readily available. Preferred polysaccharide conjugates are dextran or FICOL conjugates, more preferably a dextran conjugate.

In another embodiment of the invention, the conjugated substance is a lipid. Lipids are long-chain saturated or unsaturated aliphatic hydrocarbons (typically having 6-25 carbon atoms) and their derivatives, such as fatty acids, alcohols, amines, amino alcohols, and aldehydes. The class of lipids includes glycolipids, phospholipids and sphingolipids. Alternatively, the conjugated substance is a lipid vesicle, such as a liposome, or is a lipoprotein. Alternatively, the dye contains a lipophilic substituent, e.g. a linear saturated or unsaturated fatty alkyl group, typically with 12-18 carbon atoms.

In another embodiment of the invention, the conjugated substance is a drug or toxin. Where the conjugated substance is a drug, preferred drugs of interest are the alkaloids (including morphine alkaloids), steroids, lactams having from 5 to 6 annular members, aminoalkylbenzenes, benzheterocyclics, purines, marijuana-derived drugs, vitamins, prostaglandins, antibiotics and aminoglycosides, as well as their individual derivatives and metabolites. Metabolites related to diseased states include spermine, galactose, phenylpyruvic acid and porphyrin Type 1. Among pesticides of interest are polyhalogenated biphenyls, phosphate esters, thiophosphates, carbamates, polyhalogenated sulfenamides, their metabolites and derivatives.

The conjugated substance is optionally an ion-complexing moiety. Preferred ion-complexing moieties are crown ether, including diaryldiaza crown ethers, as described in U.S. Pat. No. 5,405,975 to Kuhn et al. (1995); derivatives of 1,2-bis-(2-aminophenoxyethane)-N,N,N',N'-tetraacetic acid (BAPTA), as described in U.S. Pat. No. 5,453,517 to Kuhn et al. (1995), U.S. Pat. No. 5,516,911 to London et al., and U.S. Pat. No. 5,049,673 to Tsien et al. (1991) (all incorporated herein by reference); derivatives of 2-carboxymethoxyaniline-N,N-diacetic acid (APTRA), as described by Ragu et al. AM. J. PHYSIOL. 256, C540 (1989); and pyridine- and phenanthroline-based metal ion chelators, as described in U.S. Pat. No. 5,648,270 to Kuhn et al. Preferably the conjugated ion-complexing moiety is a diaryldiaza crown ether chelator or a BAPTA chelator.

Conjugates of non-biological polymers are also useful aspects of the invention, including dye-conjugates of synthetic polymers, polymeric particles (including magnetic and non-magnetic microparticles) polymeric membranes, conducting and non-conducting metals and non-metals, and glass and plastic surfaces and particles. Conjugates are optionally prepared by copolymerization of a benzazole dye that contains an appropriate functionality (for example an acrylic acid- or styryl-substituent) while preparing the polymer, or more commonly by chemical modification of a polymer that contains functional groups with suitable chemical reactivity. In another embodiment of the invention, the conjugated substance is a glass or silica, which may be formed into an optical fiber or other structure. Other types of reactions that are useful for preparing dye-conjugates, especially of polymers, include catalyzed polymerizations or copolymerizations of alkenes, reactions of dienes with dienophiles, and transesterifications or transaminations.

In another aspect of the invention there are provided diagnostic assay methods including in vivo diagnostic imaging methods. The labeled conjugates of the invention may be used in any of many applications such as, for example, in diagnostic assays such as sandwich assays, competitive assays, immunometric assays or in immune response reactions employing labeled reagents.

The particular assays and methods in which the labeled conjugates of the invention find utility, e.g., immunometric assays, sandwich assays, competitive binding assays, in vivo imaging methods, etc. are well known and therefore extensive discussion of such assay and imaging methods is not required here. In such known diagnostic assays a biological reaction or interaction results in the generation of a detectable signal.

The dyes and labeled conjugates of the invention may also be used for the fluorescent staining of cells. The cells may then be observed under a microscope with the presence of the fluorescent molecule being indicative of the presence of a specific determinative site. Further, the dyes and conjugates may be used for the deletion, separation or other application in a fluorescent activated cell sorter. The fluorescent dyes can also be used for vacuolar staining of yeast and other fungi (see, for example, U.S. Pat. No. 5,445,946) and Gram reaction in bacterial populations (see, for example, U.S. Pat. No. 5,545,535). The fluorescent dyes that are able to preferentially bind to a specific biological molecule in a sample enable the determination of the presence or quantity of that specific molecule. In addition, the specific cellular structures can be monitored with respect too their spatial and temporal distribution in diverse environments. Furthermore, the dyes can be used for the determination of ionic, electrical or metabolic properties of cellular organelles (see, for example, U.S. Pat. No. 5,459,268), immunofluorescence labeling, fluorescent analog cytochemistry, vital staining of organelles, assessment of cell morphology or intracellular coupling with microinjected tracers, measurement of distances between probes by fluorescence energy transfer and measurement of diffusion coefficients and exchange rates by photobleaching recovery (see, for example, Roger Y. Tsien, Ann. Rev. Neurosci. 12, 227, 1989).

The fluorescent conjugates of organophosphorus nerve agents can be used for the screening and selection of nerve agents (Luis, Briseno-Roa et al, J. Med. Chem. 49, 246, 2006).

DEFINITIONS

The term "aryl," as used herein, refers to a mono-, bicyclic or tricyclic carbocyclic ring system having one, two or three aromatic rings including, but not limited to, phenyl, naphthyl, anthryl, azulyl, tetrahydronaphthyl, indanyl, indenyl and the like.

The term "substituted aryl," as used herein, refers to an aryl group, as defined herein, substituted by independent replacement of one or more of the hydrogen atoms thereon with substituents independently selected from substituents such as, but not limited to, alkyl, haloalkyl, alkoxy, thioalkoxy, amino, alkylamino, dialkylamino, acylamino, hydroxyl, cyano, halo, mercapto, nitro, carboxaldehyde, carboxyl, alkoxycarbonyl, carboxamide, aryl, substituted aryl, heteroaryl, substituted heteroaryl, benzyl, benzyloxy, aryloxy, heteroaryloxy, $C_1$-$C_6$-alkoxy, methoxymethoxy, methoxyethoxy, amino, benzylamino, arylamino, heteroarylamino, $C_1$-$C_3$-alkylamino, thio, aryl-thio, heteroarylthio, benzylthio, $C_1$-$C_6$-alkyl-thio, or methylthiomethyl. Representative substituents include, but are not limited to, F, Cl, Br, I, OH, $NO_2$, CN, C(O)—$C_1$-$C_6$-alkyl, C(O)-aryl, C(O)-heteroaryl, $CO_2$-alkyl, $CO_2$-aryl, $CO_2$-heteroaryl, $CONH_2$, CONH—$C_1$-$C_6$-alkyl, CONH-aryl, CONH-heteroaryl, OC(O)—$C_1$-$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$-$C_6$-alkyl, OCONH-aryl, OCONH-heteroaryl, NHC(O)—$C_1$-$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$-$C_6$-alkyl, NHCONH-aryl, NHCONH-heteroaryl, $SO_2$—$C_1$-$C_6$-alkyl, $S_2$-aryl, $SO_2$-heteroaryl, $SO_2NH$—$C_1$-$C_6$-alkyl, $SO_2NH$-aryl, $SO_2NH$-heteroaryl, $C_1$-$C_6$-alkyl, $C_3$-$C_6$-cycloalkyl, $CF_3$, $CH_2CF_3$, $CH_2Cl_2$, $CH_2OH$, $CH_2CH_2OH$, $CH_2NH_2$, $CH_2SO_2CH_3$, tetrafluorophenyl and pentafluorophenyl.

The term "heterocyclic", as used herein, refers to heterocycloalkyl and heteroaryl. The term "substituted heterocyclic", as used herein, refers to substituted heterocycloalkyl and substituted heteroaryl.

The term "heterocycloalkyl," as used herein, refers to a non-aromatic 3-, 4-, 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "substituted heterocycloalkyl", as used herein, refers to a cycloalkyl group, as defined herein, substituted by independent replacement of one or more of the hydrogen atoms therein with substituents independently selected from substituents such as, but not limited to, alkyl, haloalkyl, alkoxy, thioalkoxy, amino, alkylamino, dialkylamino, acylamino, hydroxyl, cyano, halo, mercapto, nitro, carboxaldehyde, carboxyl, alkoxycarbonyl, carboxamide, aryl, substituted aryl, heteroaryl, substituted heteroaryl, benzyl, benzyloxy, aryloxy, heteroaryloxy, $C_1$-$C_6$-alkoxy, methoxymethoxy, methoxyethoxy, amino, benzylamino, arylamino, heteroarylamino, $C_1$-$C_3$-alkylamino, thio, aryl-thio, heteroarylthio, benzyl-thio, $C_1$-$C_6$-alkyl-thio, or methylthiomethyl. Representative substituents include, but are not limited to, F, Cl, Br, I, OH, $NO_2$, CN, C(O)—$C_1$-$C_6$-alkyl, C(O)-aryl, C(O)-heteroaryl, $CO_2$-alkyl, $CO_2$-aryl, $CO_2$-heteroaryl, $CONH_2$, CONH—$C_1$-$C_6$-alkyl, CONH-aryl, CONH-heteroaryl, OC(O)—$C_1$-$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$-$C_6$-alkyl, OCONH-aryl, OCONH-heteroaryl, NHC(O)—$C_1$-$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$-$C_6$-alkyl, NHCONH-aryl, NHCONH-heteroaryl, $SO_2$—$C_1$-$C_6$-alkyl, $SO_2$-aryl, $S_2$-heteroaryl, $SO_2NH_2$, $SO_2NH$—$C_1$-$C_6$-alkyl, $SO_2NH$-aryl, $SO_2NH$-heteroaryl, $C_1$-$C_6$-alkyl, $C_3$-$C_6$-cycloalkyl, $CF_3$, $CH_2CF_3$, $CH_2Cl_2$, $CH_2OH$, $CH_2CH_2OH$, $CH_2NH_2$, $CH_2SO_2CH_3$, Tetrafluorophenyl and pentafluorophenyl.

The term "heteroaryl," as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "substituted heteroaryl," as used herein, refers to a heteroaryl group as defined herein, substituted by independent replacement of one, or more of the hydrogen atoms thereon with substituents independently selected from substituents such as, but not limited to, alkyl, haloalkyl, alkoxy, thioalkoxy, amino, alkylamino, dialkylamino, acylamino, hydroxyl, cyano, halo, mercapto, nitro, carboxaldehyde, carboxyl, alkoxycarbonyl, carboxamide, aryl, substituted aryl, heteroaryl, substituted heteroaryl, benzyl, benzyloxy, aryloxy, heteroaryloxy, $C_1$-$C_6$-alkoxy, methoxymethoxy, methoxyethoxy, amino, benzylamino, arylamino, heteroarylamino, $C_1$-$C_3$-alkylamino, thio, aryl-thio, heteroarylthio, benzyl-thio, $C_1$-$C_6$-alkyl-thio, or methylthiomethyl. Representative substituents include, but are not limited to, F, Cl, Br, I, OH, $NO_2$, CN, C(O)—$C_1$-$C_6$-alkyl, C(O)-aryl, C(O)-heteroaryl, $CO_2$-alkyl, $CO_2$-aryl, $CO_2$-heteroaryl, $CONH_2$, CONH—$C_1$-$C_6$-alkyl, CONH-aryl, CONH-heteroaryl, OC(O)—$C_1$-$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$-$C_6$-alkyl, OCONH-aryl, OCONH-heteroaryl, NHC(O)—$C_1$-$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$-$C_6$-alkyl, NHCONH-aryl, NHCONH-heteroaryl, $SO_2$—$C_1$-$C_6$-alkyl, $SO_2$-aryl, $SO_2$-heteroaryl, $SO_2NH_2$, $SO_2NH$—$C_1$-$C_6$-alkyl, $SO_2NH$-aryl, $SO_2NH$-heteroaryl, $C_1$-$C_6$-alkyl, $C_3$-$C_6$-cycloalkyl, $CF_3$, $CH_2CF_3$, $CH_2Cl_2$, $CH_2OH$, $CH_2CH_2OH$, $CH_2NH_2$, $CH_2SO_2CH_3$, tetrafluorophenyl and pentafluorophenyl.

The term "hydrophilic group" as used herein refers to a group which will improve the solubility of the molecule in water. Typical suitable hydrophilic groups which may be incorporated in the novel fluorescent compounds of the invention include: carboxylic acids (—COOH); polyethers such as those represented by —$(OCH_2CH_2)_a$—Oet where a is an integer of from 1 to 20 such as polyethylene oxide; polyalcohols which are represented by —$CH_2$—$(CHOH)_b$—$CH_2OH$, where b is an integer of from 1 to 20; primary, secondary or tertiary amines, sulfonic acids (—$SO_3H$), phosphonic acids or esters which are represented by —$(CH_2)_c$—$PO(OR_{17})(OR_{18})$ where c is an integer of from 1 to 8 and $R_{17}$ and $R_{18}$ each independently is hydrogen, alkyl, preferably having from 1 to 6 carbon atoms or aryl such as phenyl.

The term "aromatic" as used herein refers to mono cyclic planar compounds in which each atom has a p orbital which is part of a pi system with (4n+2) pi electrons, where n=0, 1, 2, 3 etc. Or a general definition is a delocalized pi cyclic system which exhibits diamagnetic ring current and in which all of the ring atoms are involved in a single conjugated system.

The term "heteroaromatic" as used herein refers to aromatic compounds with one or more elements other than carbon in the ring.

The term "aroyl" as used herein refers to a group derived from an aromatic carboxylic acid minus the carboxyl OH group.

The term "heteroaroyl" as used herein refers to a group derived from a heteroaromatic carboxylic acid minus the carboxyl OH group.

The dyes and labeled conjugates of the invention may be prepared by reactions which are known to those skilled in the art and these will be apparent from the specific synthetic preparative scheme provided below. Compounds of the invention as shown in Formula I can be synthesized as shown in the following scheme:

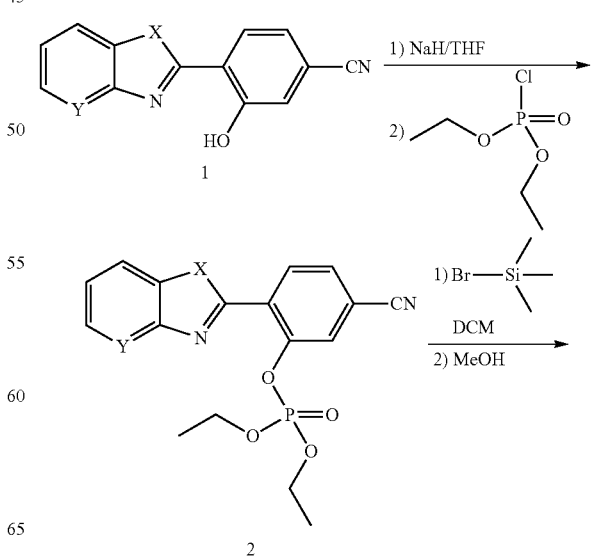

-continued

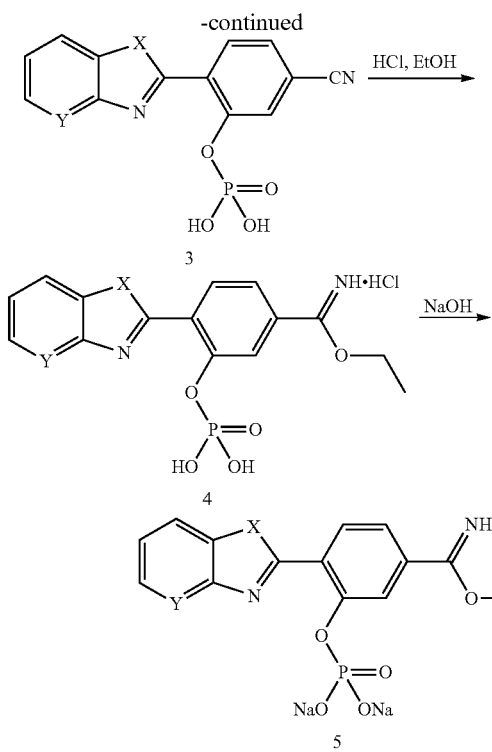

X = O, N, S, Se
Y = C, N 2-(2'-Hydroxy-4'-cyanophenyl)benzazole (1) can be made by reacting 2-hydroxy-4-cyano benzoic acid with 2-amino phenol/thiol/selenol in the presence of a cyclodehydrating agent like $PCl_3$ or $P_2O_5$ [Terashima, M et al, Synth. 484 (1982), D. W. Hein et al, J. Am. Chem. Soc. 79, 427 (1957), Freyermuth, H. B et al, U.S. Pat. No. 3,669,979 (1972)]. 1 can be converted to 3 as described by Kim, T et al [Chemical Commun. 5895 (2009)]. 3 can be converted to the benzamidic acid ethyl ester 4 by reaction with HCl in absolute ethanol. Reaction of 4 with NaOH will give the target product 5.

Compounds of the invention as shown in Formula II can be made by reacting a suitably substituted aniline with 3-hydroxy-quinoline-4-carboxylic acid in polyphosphoric acid at 120° C. for about 18 hours as shown below.

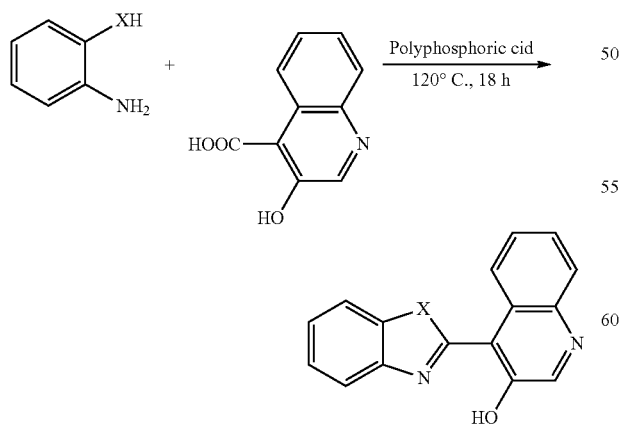

X = O, S, Se

Although the invention has been described in detail with respect to various preferred embodiments, it will be understood that these are intended to be illustrative only and the invention is not limited thereto, but rather that those skilled in the art will recognize that variations and modifications may be made therein which are within the spirit of the invention and the scope of the appended claims.

What is claimed is:

1. A dye compound represented by the formula (I)

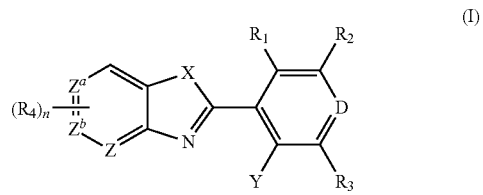

(I)

wherein
D is selected from $—C-(A)_q-R_6$, and

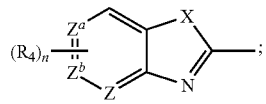

X is selected from oxygen, sulfur, selenium, and N—B,
B is selected from hydrogen, alkyl having from 1 to 10 carbon atoms, aryl, heteroaryl, acyl, aroyl having from 1 to 10 carbon atoms and heteroaroyl having from 1 to 10 carbon atoms;
Z is carbon;
$Z^a$ is selected from carbon and $—C-(A)_q-R_6$;
$Z^b$ is selected from carbon, N-alkyl and N-aryl;
A is a divalent linking group having alternating single and multiple bonds;
Y is a proton transfer group selected from one or more of the compounds selected from the group consisting of OH, $NH_2$, $—NHSO_2Ar$, $—NHSO_2OH$, $—NHC(=O)OH$, $—O(PG)$, $—N(PG)SO_2Ar$, $—N(PG)SO_2OH$, $—N(PG)C(=O)Ar$ and $—N(PG)C(=O)OH$ wherein PG is a protective group;
$R_1$, $R_2$ and $R_3$ each independently is selected from hydrogen, an electron withdrawing group and an electron releasing group; or $R_1$ and $R_2$ taken together with the carbon atoms to which they are attached represent the carbon atoms necessary to form a substituted or unsubstituted unsaturated carbocyclic or heteroaromatic ring;
$R_4$ is selected from hydrogen, an electron withdrawing group and an electron releasing group;
n is an integer of from 0 to 4;
q is 0 or 1;
$R_6$ is

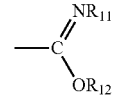

wherein the line "-" drawn on the left side of the compound represents a bond to "C" in the compound $—C-(A)_q-R_6$ when q is 0 and a bond to "A" when q is 1;

where $R_{11}$ is H, alkyl, aryl, heteroaryl;
$R_{12}$ is hydrogen, alkyl, aryl or heteroaryl; and
provided that when D is

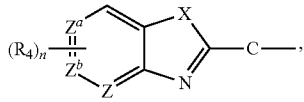

at least one of $Z^a$ is —C-(A)$_q$-R$_6$.

2. A fluorescent conjugate comprises the dye molecule of the formula

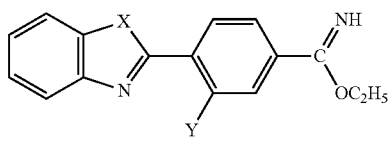

and a biological or a synthetic organic or inorganic moiety;
where X is selected from the group consisting of oxygen, sulfur, and selenium;
Y is a proton transfer group selected from one or more of the compounds selected from the group consisting of OH, NH$_2$, —NHSO$_2$Ar, —NHSO$_2$OH, —NHC(=O)OH, —O(PG), —N(PG)SO$_2$Ar, —N(PG)SO$_2$OH, —N(PG)C(=O)Ar and —N(PG)C(=O)OH wherein PG is a protective group; and wherein the group

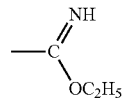

is attached to said biological or synthetic organic or inorganic moiety.

3. The fluorescent conjugate as defined in claim 2 wherein said dye molecule is attached to said biological or synthetic organic or inorganic moiety through a non-conjugated divalent achromophoric linking group.

4. The fluorescent conjugate as defined in claim 3 wherein said biological moiety is an amino acid or a polymer of amino acids.

5. The fluorescent conjugate as defined in claim 3 wherein said biological moiety is selected from a nucleic acid base, a nucleoside, a nucleotide and a nucleic acid polymer.

6. A fluorescent conjugate as defined in claim 3 wherein said biological moiety comprises a nucleic acid polymer having fewer than 50 nucleotides.

7. The fluorescent conjugate as defined in claim 3 wherein said biological moiety is a carbohydrate or a lipid moiety.

8. The fluorescent conjugate as defined in claim 3 wherein said biological or synthetic organic or inorganic moiety is a drug or a toxin.

* * * * *